United States Patent
Sashidhara et al.

(10) Patent No.: US 8,921,417 B2
(45) Date of Patent: Dec. 30, 2014

(54) METHOD OF TREATING DYSLIPIDEMIA USING NATURALLY OCCURRING DITERPENE

(75) Inventors: Koneni Venkata Sashidhara, Uttar Pradesh (IN); Anju Puri, Uttar Pradesh (IN); Jammikuntla Naga Rosaiah, Uttar Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 948 days.

(21) Appl. No.: 12/323,156

(22) Filed: Nov. 25, 2008

(65) Prior Publication Data
US 2009/0247626 A1    Oct. 1, 2009

(30) Foreign Application Priority Data
Mar. 26, 2008   (IN) .............................. 773/DEL/2008

(51) Int. Cl.
*A61K 31/365* (2006.01)
*C07D 307/60* (2006.01)

(52) U.S. Cl.
CPC ............ *A61K 31/365* (2013.01); *C07D 307/60* (2013.01)
USPC ....................................................... 514/473

(58) Field of Classification Search
None
See application file for complete search history.

(56) References Cited

U.S. PATENT DOCUMENTS

2009/0291155 A1* 11/2009 Chauhan et al. .............. 424/725

OTHER PUBLICATIONS

"Clerodate Diterpenoids from Polyalthia Longifolia" by Phadnis et al., Phytochem. 27, 2899-901 (1988).*
"Structural mechanism for statin inhibition of 3-hydroxy-3-methylglutaryl coenzyme A reductase" by Istvan, Am. Heart J. 114, S27-32 (2002).*
"Drug Treatment of Dyslipidemia" in Goodman & Gilman's The Pharmacological Basis of Therapeutics, 11th Ed., by Shanahan et al. (Eds.), McGraw-Hill (New York), pp. 948-953 (2006).*
K. Andersen et al. (1987), "Cholesterol and Mortality: 30 years of Follow-up from the Framingham Study," *JAMA*, vol. 257, pp. 2176-2180.
C. Ichino, et al. (2006), "Short Communication: Screening of Thai Medicinal Plant Extracts and Their Active Constituents for In Vitro Antimalarial Activity," *Phytotheraphy Research* 20, pp. 307-309, 2006.
Eghdamian et al. (1998), "Mode of Action and Adverse Effects of Lipid Lowering Drugs," *Drugs Today*, 34, pp. 943.

F. Rizvi et al. (2003), "Antidyslipidemic action of fenofibrate in dyslipidemic-diabetic hamster model," *Biochem. Biophys. Res. Commun.*, 305, pp. 215.
M.A. Rashid et al. (1996), "Short Communication: Antimicrobial Diterpenes from *Polyalthia longifolia* var. *pendulla* (*Annonaceae*)," *Phytotheraphy Research* 10, pp. 79-81.
X. Ma et al. (1994), "Cytotoxic Clerodane Diterpenes from *Polyalthia barnesii*," *Phytochemistry*, vol. 37, pp. 1659-1662.
Hanson (2011), "Diterpenoids of terrestrial origin," Nat. Prod. Rep., 2011, 28, 1755.
Hanson (2007), "Diterpenoids," Nat. Prod. Rep., 2007, 24, 1332-1341.
Manzoni and Rollini (2002), "Biosynthesis and biotechnological production of statins by filamentous fungi and application of these cholesterol-lowering drugs," Appl Microbiol Biotechnol, 2002, 58, 555-564.
Merrit and Ley (1992), "Clerodane Diterpenoids," Nat. Prod. Rep., 1992, 9, 243-287.
Radha and Lakshmanan (2013), "A Review: Lovastatin Production and Applications," Asian J Pharm Clin Res, 2013, 6(3), 21-26.
Sashidhara (2011), "Discovery of a new class of HMG—CoA reductase inhibitor from *Polyalthia longifolia* as potential lipid lowering agent," European Journal of Medicinal Chemistry, 2011, 46, 5206-5211.
Sviridov et al. (1990), "Inhibition of cholesterol synthesis and esterification regulates high density lipoprotein interaction with isolated epithelial cells of human small intestine," Journal of Lipid Research, 1990, 31, 1821-1830.

* cited by examiner

*Primary Examiner* — Theodore R West
(74) *Attorney, Agent, or Firm* — Lathrop & Gage LLP

(57) ABSTRACT

A method for treatment and or/prevention of dyslipidemia is provided. The invention relates to reducing low density lipoprotein cholesterol concentration by using naturally occurring diterpene (16α-hydroxycleroda-3,13(14)Z-dien-15,16-olide, a compound having formula (1)) isolated from leaves of *Polyalthia longifolia*.

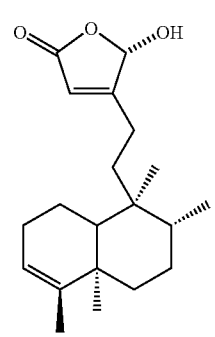

Formula-1

$C_{20}H_{30}O_3$
Exact Mass: 318.22
Mol. Wt.: 318.45

14 Claims, 1 Drawing Sheet

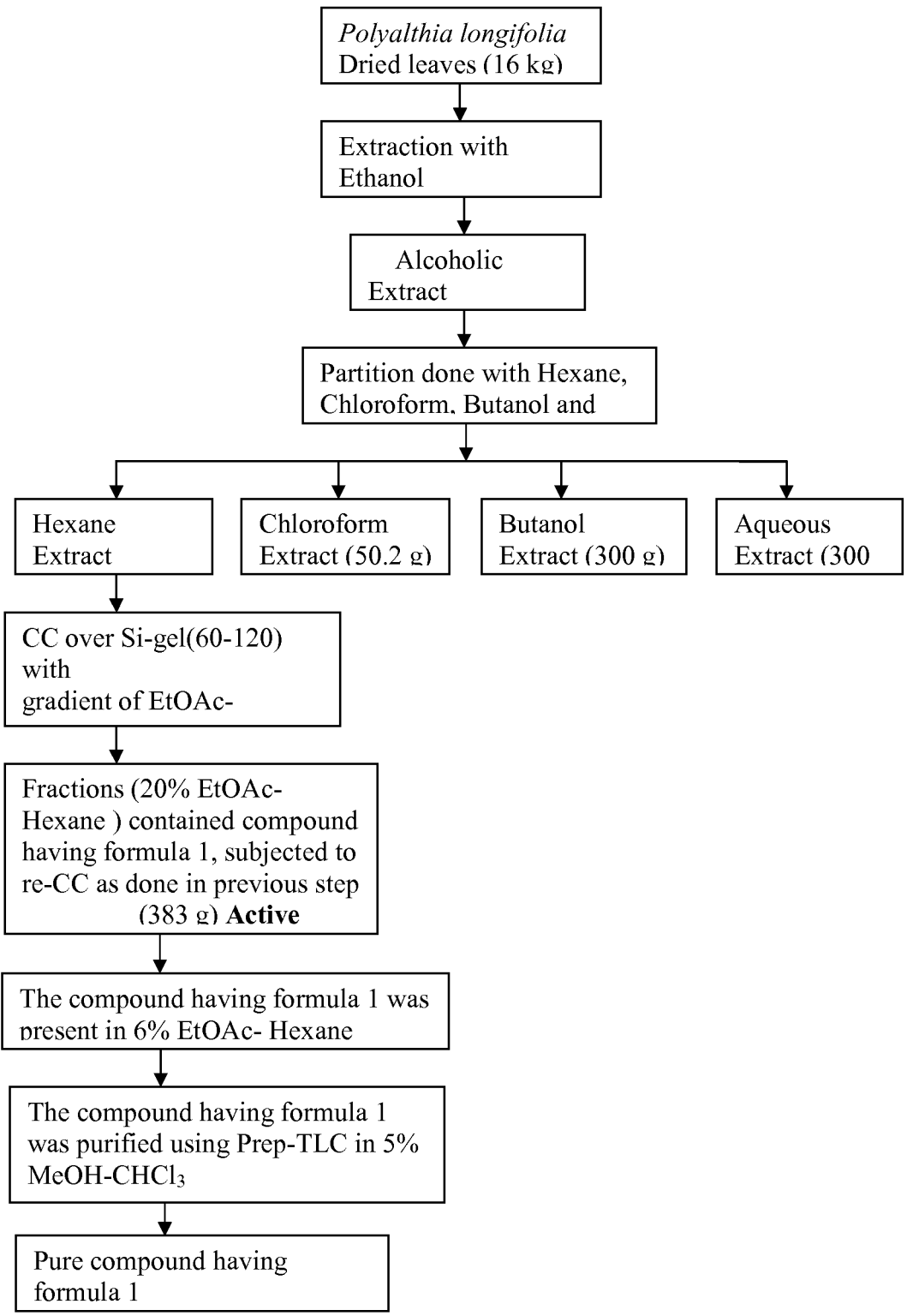

METHOD OF TREATING DYSLIPIDEMIA USING NATURALLY OCCURRING DITERPENE

CROSS-REFERENCE TO RELATED APPLICATIONS

This application claims priority to Indian Patent Application No. 773/DEL/2008 filed Mar. 26, 2008, which is incorporated herein by reference to the extent not inconsistent herewith.

BACKGROUND

Atherosclerosis, the principal contributor to the pathogenesis of myocardial and cerebral infarction, is known to be one of the leading causes of morbidity and mortality worldwide. Elevated plasma concentration of cholesterol, especially low density lipoprotein (LDL) and triglyceride is recognized as a leading cause in the development of atherosclerosis and coronary heart disease. (Cholesterol and Mortality: 30 years of Follow-up from the Framingham Study, Anderson, Castelli, & Levy, JAMA, Vol. 257, pp. 2176-80 (1987). These conditions are responsible for one-third of deaths in industrialized nations. (Eghdamian, E.; Ghose, K. Drugs Today, 1998, 34, pp. 943.)

Several drugs are being used in the treatment of dyslipidemia. The drugs can intervene by lowering cholesterol (LDL and total cholesterol) or by lowering triglyceride levels in plasma. Treatment of hyperlipidemia using statins has been used to lower serum levels of cholesterol and triglyceride. Statins such as atorvastatin, lovastatin, fluvastatin, simvastatin and pravastatin are HMG CoA reductase inhibitors which act by inhibiting cholesterol synthesis and upregulate LDL receptors in livers. However, common side effects of statins are myositis, arthralgias, gastrointestinal upset and elevated liver function tests. The fibric acid derivatives, e.g., Clofibrate, gemfibrozil, fenofibrate and ciprofibrate, stimulate lipoprotein lipase that breaks down lipids in lipoproteins and may decrease very low density lipoproteins (VLDL) synthesis. Fibric acid derivatives are used to treat elevated triglyceride levels and among the side effects are myositis, gastrointestinal upset, gallstones and elevated liver function tests. Other drug types used for treatment of hyperlipidemia are bile acid binding resins e.g. cholestyramine and cholestipol. Bile acid binding resins promote bile acid secretion and they increase LDL receptors in the liver. Common side effects are bloating, constipation and elevated triglycerides. Also, Nicotinic acid decreases VLDL synthesis and is used for treatment of elevated LDL and VLDL. Among the prominent side effects of nicotinic acid are cutaneous flushing, gastrointestinal upset, abnormality in liver, elevated glucose and uric acid. Thus, there is a need for the therapeutic benefits of several anti-dyslipidemic drugs while simultaneously reducing the severe side effects.

All publications referred to herein are incorporated herein to the extent not inconsistent herewith for purposes of enablement and written description.

SUMMARY

The present invention relates to method for treatment and or/prevention of dyslipidemia. More specifically, the invention relates to reducing low density lipoprotein cholesterol concentration by using naturally occurring diterpene (16α-hydroxycleroda-3,13(14)Z-dien-15,16-olide, formula 1) isolated from leaves of *Polyalthia longifolia*.

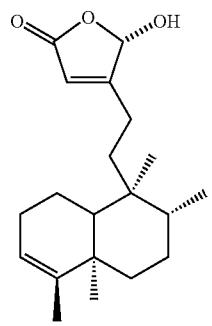

Formula-1

$C_{20}H_{30}O_3$
Exact Mass: 318.22
Mol. Wt.: 318.45

*Polyalthia longifolia* var. *pendula* (locally known as ulta Asoka) family annonaceae is an evergreen ornamental tree which is widely distributed in southern Taiwan, Pakistan, Bangladesh, Sri Lanka and temperate regions of India.

As a part of our drug discovery program on Indian medicinal plants, we have recently discovered the antidyslipidemic activity in the alcoholic extract and its hexane fraction of the leaves of *Polyalthia longifolia*. Further bioactivity directed fractionation work on the plant led to isolation of pure compound 16α-hydroxycleroda-3,13(14)Z-dien-15,16-olide and also to discover its antidyslipidemic activity. This compound has earlier been reported for in vitro anti-malarial activity, (C. Ichino, et al., *Phytotheraphy Research* 20, pp. 307-309, 2006), cytotoxicity (X. MA et al., *Phytochemistry*, vol. 37, pp. 1659-1662, 1994) and antimicrobial activity (M. A. Rashid, et al., *Phytotheraphy Research* 10, pp. 79-81, 1996.

The molecule of the present invention has the following spectral characteristics:
$[\alpha]_D$: $-68.92°$ (MeOH, c 0.0304), UV $\lambda_{max}$ (MeOH): 210 nm (log ε4.1), IR $v_{max}$(neat) cm$^{-1}$: 3379, 2935, 1752, 1647, 1457, 1382, 1131, 953, 757, ESIMS: m/z (rel. int.) 318[M$^+$] (13), $^1$H NMR(CDCl$_3$, 300 MHz): δ 1.52 (2H, m, H-1), 2.04 (2H, m, H-2), 5.18 (1H, brs, H-3), 1.75 (1H, m, H-6a), 1.18 (1H, m, H-6b), 1.44 (2H, m, H-7), 1.45 (1H, m, H-8),1.34 (1H, m, H-10), 1.70 (1H, m, H-11a), 1.52 (1H, m, H-11 b), 2.26 (2H, m, H-12), 5.85 (1H, s, H-14), 6.07 (1H, s, H-16), 0.81 (3H, d, J=6.42 Hz, H-17),1.58 (3H, s, H-18), 1.00 (3H, s, H-19), 0.77 (3H, s, H-20), $^{13}$C NMR(CDCl$_3$, 75 MHz): δ 18.47 (C-1), 26.97 (C-2),120.58 (C-3), 144.51 (C-4), 38.36 (C-5), 36.92 (C-6), 27.57 (C-7), 36.53 (C-8), 38.87 (C-9), 46.68 (C-10), 35.06 (C-11), 21.59 (C-12), 170.43 (C-13), 117.65 (C-14), 172.03 (C-15), 101.85 (C-16), 16.15 (C-17), 18.13 (C-18), 20.08 (C-19), 18.35 (C-20).

The isolated compound having formula (1) showed significant antidyslipidemic activity in high fat diet (HFD) fed dyslipidemic hamsters at different doses of body weight. The high fat diet (HFD) fed dyslipidemic hamster model has been reported as an ideal in vivo model for evaluating antidyslipidemic drugs. (F. Rizvi et al., Biochem. Biophys. Res. Commun. 2003,305, pp. 215).

Neither the plant nor the compound having formula (1) is known for this anti-dyslipidemic activity hitherto. This known compound having formula (1) is obtained in good yield (0.28%) from leaves (renewable source) of *Polyalthia longifolia* and this plant is available in India in abundance.

Provided herein is a method of treatment of dyslipidemia by administering to a patient in need thereof a naturally occurring compound represented by formula (1), which is isolated from the leaves of *Polyalthia longifolia* belonging to the family Annonaceae.

BRIEF DESCRIPTION OF THE FIGURE

FIG. 1 is a flow chart showing a process for extraction of the compound of Formula 1 from *Polyalthia longifolia* leaves.

DETAILED DESCRIPTION

A method is provided for treating and or prevention of dyslipidemia in a subject comprising administering to the subject a therapeutically effective amount of a compound of

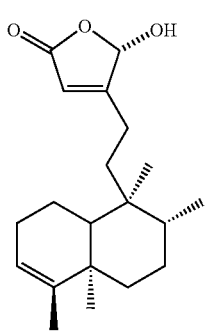

Formula-1

In an embodiment the compound of Formula 1 or an extract containing compound of formula 1 isolated from *Polyalthia longifolia* can be used to minimize the development of atherosclerosis.

In another embodiment the effective dose of the compound is ranging between 5 to 100 mg/kg. (Activity was tested at 5, 10, 25, 50, 100 mg/Kg body weight dose, by mouth (p.o.), for seven consecutive days.)

In yet another embodiment the compound is effective in lowering the triglycerides (TG) up to 51% at a dose of 25 mg/kg body weight. (Highest triglyceride lowering at 25-mg/Kg doses).

In an embodiment the compound is effective to reduce total cholesterol (TC) by 23% to 55% at a dose in the range of 5 to 100 mg/kg.

In a further embodiment the compound is effective to increase HDL/TC ratio up to 54% at a dose of 5 to 100 mg/kg body weight.

In still another embodiment the subject is any rodent or mammal including human being.

In an embodiment the compound is isolated from any plant containing it or synthetically prepared.

In an embodiment the compound is isolated from *Polyalthia longifolia*.

In an embodiment the extract is an ethanolic extract or hexane soluble fraction extract prepared from the leaves of *Polyalthia longifolia*.

In an embodiment the ethanolic extract is effective in lowering of plasma levels of triglyceride (TG) 35%, cholesterol 14% and glycerol (Gly) 36%, accompanied by increase in high density lipoprotein cholesterol (HDL-C)/TC ratio 12% at dose of 500 mg/kg.

In an embodiment the hexane-soluble fraction is effective to decrease serum TG by 54%, total cholesterol (TC) by 49% and glycerol (Gly) by 55%, in high fat diet (HFD)-fed dyslipidemic hamsters at a dose of 100 mg/kg.

Accordingly, provided herein is a simple method of treatment of dyslipidemia by administering to a patient in need thereof a naturally occurring compound represented by formula (1) which is isolated from the leaves of *Polyalthia longifolia* belonging to the family Annonaceae.

The isolation of the compound comprises the following steps:
(i) extracting the dried and pulverized leaves of the plant with alcohol at 20-40° C. and concentrating the solvent to obtain an alcoholic extract;
(ii) partitioning the alcoholic extract between hexane, chlorinated solvent, butanol and water, then concentrating the different extracts under reduced pressure;
(iii) adsorbing the hexane extract with an adsorbent such as silica gel and drying the adsorbed material at a temperature ranging from 20-50° C. for 1-2 hours;
(iv) extracting the adsorbed material with a non-polar solvent mixed with varying proportions of a polar solvent; and
(v) concentrating the fractions containing the compound represented by formula (1) to a residue; with further purification using preparative thin layer chromatography/HPLC.

The pure compound thus isolated by activity-directed fractionation led to discovery of its anti-dyslipidemic principles.

In an embodiment the non polar solvent used in the process as stated above is selected from the group consisting of hexane, diethyl ether, and dichloromethane.

In an embodiment the polar solvent used in the process as stated above is selected from the group consisting of ethyl acetate, ethanol, and methanol.

A pharmaceutical composition is prepared using the compound of formula 1 or the extract wherein the composition comprises a therapeutically effective amount of a compound of formula 1 or an extract containing compound of formula 1 isolated from *Polyalthia longifolia* optionally along with a pharmaceutically acceptable carrier, excipient, and/or diluent.

EXAMPLES

The invention is described in detail in the examples given below which are provided to illustrate the invention and therefore should not be construed to limit the scope of the present invention.

Experimental Methodology for Biological Activity

Male golden Syrian hamsters weighing 110-120 g were divided into hyperlipidemic and hyperlipidemic plus drug-treated groups. Each group consisted of eight animals. Hyperlipidemia was produced by feeding with a high fat diet (HFD). Hyperlipidemic hamsters had free access to the HFD and water ad lib during the entire period of the experiment. The test samples were given orally at the dose mentioned using water as a drug vehicle from day 4 to day 10 (7 days) in the HFD fed hamsters.

Normal hamsters fed with the HFD and given the drug vehicle (water) only served as control animals. Body weight and diet intake of each animal group was recorded daily to check the effect of the drug on food intake and body weight of the animals. At the end of the experiment, i.e., on the $10^{th}$ day, the blood of the non-fasted animals was withdrawn in EDTA coated tubes and the tubes were cooled to 4° C. for 15 min. The cold plasma was separated and biological analysis of the plasma was performed on the same day using commercially available enzymatic diagnostic kits for triglycerides (TG), total cholesterol (TC), high density lipoprotein (HDL), glycerol (GLY) and low density lipoprotein (LDL) using a Synchron CX-5 Clinical System, Beckmann Coulter Instrument. The data was analyzed for its significance on Prism Software.

In an embodiment, the crude alcoholic extract of the leaves can be used to treat dyslipidemia at a dose of 500 mg/kg in high fat diet-fed hamster model.

Percentages of the ingredients in the alcoholic fraction are as follows: 16α-hydroxycleroda-3,13(14)Z-dien-15,16-olide (2.27%), 16-oxocleroda-3,13(14)E-dien-15-oic acid (0.185%), 3β,16α-dihydroxycleroda-4(18), 13(14)Z-dien-15,16-olide (0.221%), (4→2)-abeo-16(R/S)-2,13Z-Kolavadien-15,16-olide-3-al (0.170%), 3,12E-Kolavadien-15-oic acid-16-al (0.032%) and labd-13E-en-8-ol-15-oic acid (0.056%).

In another embodiment hexane extract of the leaves can be used to treat dyslipidemia at a dose of 100 mg/kg in high fat diet-fed hamster model.

In yet another embodiment the pure isolated compound from the hexane extract at different doses (5, 10, 25, 50, 100 mg/kg) of body weight significantly decreased serum TG, total cholesterol (TC), and glycerol (Gly), accompanied by increase in HDL-C/TC ratio in high fat diet-fed dyslipidemic hamsters.

Example 1

Air-dried ground leaves of *P. longifolia* var. *pendula* were extracted with ethanol (50 L, three times) for three consecutive days at room temperature. Evaporation of the solvent under reduced pressure yielded ethanolic extract (2 Kg). This ethanolic extract was macerated with hexane (2 L, three times) and the remaining residue dissolved in water (2 L) and partitioned with chloroform (2 L, three times) and butanol (2 L, three times) to yield three fractions, which on concentration under reduced pressure at water bath temperature 20-50° C.; yielded hexane extract (1.2 Kg), chloroform extract (50.2 gm) and butanol extract (300 gm).

Example 2

The hexane extract (1.2 Kg) was subjected to silica gel (60-120 mesh) column chromatography using EtOAc: Hexane gradient (0:100 to 100:0) and finally washed with methanol, and gave eight major sub-fractions. The compound represented by formula 1 was present in 20% EtOAc: Hexane fraction (383 gm).

Isolation of the compound represented by the formula 1 is as follows: A part of the 20% EtOAc: Hexane fraction (30 gm) was further taken up for the separation of diterpenes. It was chromatographed over flash silica gel (230-400 mesh) with a hexane-EtOAc gradient (100:0 to 0:100) to furnish eight sub-fractions. Fraction III (4% EtOAc: Hexane fraction), contained an impure compound (0.850 gm) which was purified by preparative thin layer chromatography (TLC) using MeOH: CHCl$_3$ (5:95) as a mobile phase to give 16-oxocleroda-3,13(14)E-dien-15-oic acid (0.29 gm). Fraction IV (6% EtOAc: Hexane fraction, 6.5 gm) was similarly purified to give 16α-hydroxycleroda-3,13(14)Z-dien-15,16-olide (3.56 gm). Fraction VI (8% EtOAc: Hexane fraction, 1.3 gm) was chromatographed over flash silica gel using Acetone: Benzene (0:100 to 50:50) to furnish two major fractions. The second fraction was again re-chromatographed over flash silica gel with Acetone: Benzene (1:99) as the eluent, to furnish pure 3,12E-Kolavadien-15-oic acid-16-al (0.05 gm). Fraction VII (10%-15% EtOAc: Hexane fraction, 1.3 gm) was then purified through column chromatography, firstly using EtOAc:Hexane (0:100 to 30:70) and then with MeOH: Benzene (0.5:99.5) as the mobile phase to furnish pure crystals of Labd-13E-en-8-ol-15-oic acid (0.088 gm). Fraction VIII (15% EtOAc: Hexane fraction, 4.2 gm) was re-chromatographed on silica gel (100-200 mesh) with EtOAc: Hexane gradient (5:95 to 50:50) to give three fractions. Fraction A (0.877 gm), contained a strongly u.v. (254 nm) active compound, which was purified by preparative HPLC (reverse phase column, YMC-Pack ODS-A, 250×20 mm I.D., S-5 μm, 12 nm, gradient: MeOH:H$_2$O—30:70 to MeOH:H$_2$O—70:30 in 30 min at a flow rate of 5 ml per min, at $\lambda_{max}$; 210 nm and 235 nm) to give (4→2)-abeo-16(R/S)-2,13Z-Kolavadien-15,16-olide-3-al (0.266 gm). Fraction C (0.570 gm), which was then subjected to flash CC (230-400 mesh), elution done with EtOAc: Hexane (15:85), which was changed to EtOAc: Hexane (20:80) after running 500 ml of the solvent. The middle fifteen fractions on concentration yielded 3β,16α-dihydroxycleroda-4(18), 13(14)Z-dien-15,16-olide (0.346 gm).

Example 3

Activity of Crude Extract of *Polyalthia longifolia*

Oral administration with ethanolic extract of *Polyalthia longifolia* at a dose of 500 mg/kg body weight for 7 days, in dyslipidemic hamsters resulted in significant lowering of plasma levels of triglyceride (TG) 35%, cholesterol 14% and glycerol (Gly) 36%, accompanied by increase in HDL-C/TC ratio of 12%. Ethanolic extract was fractionated into hexane, chloroform, n-butanol and water-soluble fractions, which were evaluated. Activity was proved to be concentrated in the hexane-soluble fraction, which at a dose of 100 mg/kg body weight, significantly decreased serum TG by 54%, total cholesterol (TC) by 49% and glycerol (Gly) by 55%, in high fat diet (HFD)-fed dyslipidemic hamsters.

Example 4

Antidyslipidemic Activity of the Isolated Compound of Formula (1) at a Dose of 25, 50, 100 mg/kg The compound of formula (1) obtained from the leaves was administered orally at the dose of 25 mg/kg body weight for seven consecutive days.

The compound of formula (1) at the dose of 25 mg/kg body significantly lowered the serum TG by 51%, total cholesterol (TC) by 46%, glycerol (Gly) by 51%, and Low density lipoproteins (LDL) by 49%, accompanied by increasing HDL/TC by 36% in the high fat diet (HFD)-fed dyslipidemic hamster model.

The compound of formula (1) at the dose of 50 mg/kg body has significantly lowered the serum TG by 46%, total cholesterol (TC) by 55%, glycerol (Gly) by 48%, and Low density lipoproteins (LDL) by 41%, accompanied by increasing HDL/TC by 54% in the high fat diet (HFD)-fed dyslipidemic hamster model.

The compound of formula (1) at the dose of 100 mg/kg body has significantly lowered the serum TG by 43%, total cholesterol (TC) by 54%, glycerol (Gly) by 43%, and Low density lipoproteins (LDL) by 65%, accompanied by increasing HDL/TC by 46% in high fat diet (HFD)-fed dyslipidemic hamster model.

The results obtained in dyslipidemic hamsters showed a significant decrease in lipid profile. Elevated triglyceride levels increase the risk of coronary heart disease (CHD); in contrast, high density lipoproteins (HDL) mediate the reverse transport of cholesterol from peripheral tissues to the liver, which will disallow the slow accumulation of lipids in artery walls.

The reference drug fenofibrate lowered the TG by 42%, TC by 18%, Gly by 36%, and increased the HDL-C/TC by 10% in our experiments at a dose of 108 mg/kg body weight in the same hamster model.

Lovastatin in the same model, at a dose of 25 mg/kg of body weight, lowered the serum TG by 29%, total cholesterol (TC) by 9%, glycerol (Gly) by 35%, accompanied by increasing HDL/TC by 12% in the high fat diet (HFD)-fed dyslipidemic hamster model.

Atorvastatin at a dose of 10 mg/kg lowered the TG by 63%, TC by 14%, Gly by 52%, and increased the HDL/TC by 35% in our experiments in the same hamster model.

The compound represented by Formula 1 is found to have an unexpected advantage over these known drugs, Lovastatin and Atorvastatin, as both of these drugs lowered the TC plasma concentration by only 9% and 14% respectively, while the compound of formula (1) lowered TC up to 55% in the HFD-fed hamster model.

The compound having formula (1) is effective over a wide dosage range.

TABLE 1

Antidyslipidemic activity of Compound 1 isolated from *Polyalthia Longifolia*

| Group | DOSE (mg/kg) | TG (mM) | TC (mM) | GLY (mM) | LDL (mM) | HDL/TC |
|---|---|---|---|---|---|---|
| Compound 1 | 5 | −19 | −27* | −10 | — | +12 |
|  | 10 | −26*** | −23* | −5 | — | +12 |
|  | 25 | −51*** | −46** | −51*** | −49* | +36 |
|  | 50 | −46** | −55*** | −48** | −41* | +54 |
|  | 100 | −43** | −54*** | −43*** | −65*** | +46 |
| (Standard Drug) | | | | | | |
| Lovastatin | 25 | −29 | −9 | −35 | — | +12 |
| Atorvastatin | 10 | −63*** | −14 | −52* | — | +35 |

Values are percent changes with respect to HFD-fed hamster group (group of eight animals each)
*p < 0.05,
**p < 0.01,
***p < 0.001.

Advantages of the Invention:
1. Naturally occurring, plant-based compound, which can reduce levels of lipid in plasma.
2. Discovery of dyslipidemic activity from this plant and compound.
3. Isolation from a renewable source such as leaves in quantitative yields (0.28%) so the technology is ecologically safe and commercially viable.
4. The plant is very commonly available in India and thus raw material is not a problem for commercial up-scaling.
5. The biological activity is highly significant based on in vivo data in a hamster model.

Although the description herein contains many specificities, these should not be construed as limiting the scope of the invention but as merely providing illustrations of some of the presently preferred embodiments of the invention. For example, thus the scope of the invention should be determined by the appended claims and their equivalents, including homologues and analogues of the compound depicted in Formula 1, rather than by the examples given.

The invention claimed is:
1. A method of treating dyslipideamia comprising administering to a subject having elevated plasma levels of triglycerides (TG), total cholesterol (TC), low density lipoprotein (LDL), or combinations thereof, a therapeutically effective amount of a compound of Formula 1:

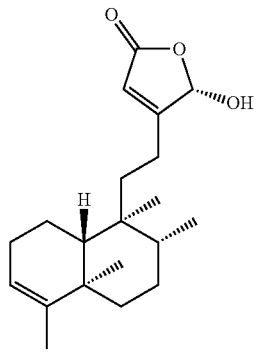

a pharmaceutically acceptable salt thereof, or an extract containing the compound of formula 1 isolated from *Polyalthia longifolia*.

2. A method according to claim 1 wherein the subject has atherosclerosis.

3. A method according to claim 1 wherein the effective dose of the compound ranges between 5 to 100 mg/kg body weight, and is administered by mouth (p.o.), for seven consecutive days.

4. A method according to claim 1 wherein the compound lowers the triglycerides (TG) in the subject up to 51% at a dose of 25 mg/kg body weight.

5. A method according to claim 1 wherein the compound reduces total cholesterol (TC) in the subject by 23% to 55% at a dose in the range of 5 to 100 mg/kg.

6. A method according to claim 1 wherein the compound increases the high-density lipoprotein/total cholesterol (HDL/TC) ratio in the subject up to 54% at a dose ranging between 5 and 100 mg/kg body weight.

7. A method according to claim 1 wherein the subject is a mammal.

8. A method according to claim 1 wherein the compound is isolated from a plant containing said compound or synthetically prepared.

9. A method according to claim 1 wherein the extract is an ethanolic extract or a hexane-soluble fraction extract prepared from the leaves of *Polyalthia longifolia*.

10. A method according to claim 1 wherein the extract isolated from *Polyalthia longifolia* comprises 16α-hydroxyclueroda-3,13(14)Z-dien-15, 16-olide as the major constituent.

11. A method according to claim 9 wherein the ethanolic extract lowers plasma levels of triglyceride (TG) by 35%, cholesterol by 14% and glycerol (Gly) by 36%, accompanied by increasing the high-density lipoprotein cholesterol/total cholesterol (HDL-C/TC) ratio in the subject by 12% at a dose of 500 mg/kg.

12. A method according to claim 9 wherein the hexane-soluble fraction decreases serum TG by 54%, total cholesterol (TC) by 49% and glycerol (Gly) by 55%, in high fat diet (HFD)-fed dyslipidemic hamsters at a dose of 100 mg/kg.

13. A method according to claim 7 wherein the subject is a human being.

14. A method according to claim 7 wherein the subject is a rodent.

* * * * *